United States Patent [19]

Oikawa et al.

[11] 4,259,321
[45] Mar. 31, 1981

[54] COMPOSITIONS AND METHODS FOR CONTROLLING COCCIDIOSIS

[75] Inventors: Hiroshi Oikawa, Kusatsu; Ken Katagiri, Ikeda; Harumoto Kawaguchi, Mie; Tetsuo Kitabatake, Kobe; Koji Nakamoto, Higashiosaka, all of Japan

[73] Assignee: Shionogi & Co., Ltd., Osaka, Japan

[21] Appl. No.: 60,057

[22] Filed: Jul. 24, 1979

[30] Foreign Application Priority Data

Aug. 11, 1978 [JP] Japan .................................. 53-98455

[51] Int. Cl.³ ............................................. A61K 31/34
[52] U.S. Cl. .................................... 424/120; 424/278
[58] Field of Search ................................ 424/120, 278

[56] References Cited

PUBLICATIONS

Mitrovic et al., Poultry Science, vol. 53, pp. 1448 to 1455, (1974).
Ishiguro, Chem. Abst., vol. 88, Abst. 184665s, (1978), (Abst. of Japan Kokai No. 78 20,420).
Ishiguro, Chem. Abst., vol. 88, Abst. 165501u, (1978), (Abst. of Ger. Offen. No. 2,735,409).
Tsuji et al., The Journal of Antibiotics, vol. 29, pp. 10 to 14, (1976).
Westley, Chem. Abstracts, vol. 84, Abst. No. 57385t, (1976), (Abst. of Ger. Offen. No. 2,514,215).
Ishida et al., Chem. Abstracts, vol. 80, Abst. 21801c, (1977), (Abst. of Japan Kokai No. 76 104,018).
Shiro et al., J. Chem. Soc. Chem. Comm., 1978, pp. 682–683.
Occolowitz et al., J. Chem. Soc. Chem. Comm., 1978, 683–684.

*Primary Examiner*—John D. Randolph
*Attorney, Agent, or Firm*—Wenderoth, Lind & Ponack

[57] ABSTRACT

Compositions and methods for the control of coccidiosis using antibiotic K-41 and its non-toxic salts as the active anti-coccidial agent.

8 Claims, No Drawings

COMPOSITIONS AND METHODS FOR CONTROLLING COCCIDIOSIS

This invention relates to compositions to control coccidiosis comprising antibiotic K-41 and its non-toxic salts as the active ingredient. Further, it relates to methods for control of coccidiosis using the above compositions. The compositions are used for prevention and treatment of coccidiosis.

Coccidiosis is a common widespread poultry disease caused by protozoa of the Genus Eimeria such as *E. tenella, E. necatrix, E. acervulina* and the like. One or more species of the protozoa infect and cause poultry to have diarrhoea and lesion of digestive organ leading to malnutrition, growth retardation and finally to death. The term 'poultry' herein used includes, for example, chicken, turkey, duck and the like. The economic loss by this infection can not be overlooked.

Compounds heretofore used as anti-coccidial agents include sulfonamides, quinolines, anti-thiamine agents, antibiotics and the like. These known anti-coccidial agents, however, suffer from some drawbacks in anti-coccidial activity and toxicity. Further, the appearance of resistant strains is an unavoidable problem. Therefore, it is strongly desired to create a new powerful anti-coccidial agent with low toxicity, hardly producing resistant strains. Antibiotic K-41 was found to satisfy the requirement and studied to be made as an anti-coccidial agent. Several antibiotics have already been used as an effective ingredient of anti-coccidial compositions. Haney et al., U.S. Pat. No. 3,501,568 (Mar. 17, 1970), for example, teaches the use of antibiotic A3823 known as monensin to prevent the development of coccidiosis in poultry. Lasalocid is disclosed in Poultry Science 53, 1448 (1974) and salinomycin is in Poultry Science 56, 926 (1977).

The antibiotic K-41 is a superior anti-coccidial agent in its powerful activity and low toxicity and the compositions containing K-41 can be used to prevent and treat coccidiosis in poultry.

The antibiotic K-41 is a polyether produced by *Streptomyces hygroscopicus* (ATCC No. 31,227, FERM-P No. 1342). The preparation and properties are described in Japanese Patent Publication Specification (Examined) No. 1977/21077 and J. Antibiotics 29, 10–14 (1976). The principal physicochemical properties of its sodium salt are as follows:

Elemental analysis: C, 58.50; H, 8.28; O, 30.49; Na, 2.73%.

Molecular weight: 1039 (by osmometry in chloroform).

Molecular formula: $C_{48}H_{81}O_{19}Na$ (by $^{13}C$ NMR spectrum and elemental analysis).

Melting point: 196°–198° C.

Specific rotation: $[\alpha]_D^{23} + 1.9 \pm 0.4$ (c = 1.017 methanol).

The $LD_{50}$ values of acute toxicity in mice are 47.4 mg/kg when intraperitoneally injected, 506.6 mg/kg orally and more than 1,000 mg/kg subcutaneously.

In anti-coccidial compositions, K-41 may be used singly or in combination with appropriate carriers ordinarily used in this field. The ordinary additives, vehicles, disintegrating agents, lubricants, stabilizers, flavourings, wetting agents, coloring agents, preservatives, aromatics and coating materials can also be combined therewith.

The composition can be prepared in the form of powders, granules, solutions, suspensions, dispersions, premixes, capsulates, emulsions, tablets and the like. If carrier is employed, a diluent ordinarily added to poultry feed may be used, for example, water, lactose, sucrose, talc, colloidal silica, soybean cake, starch, yeast, wheat, rice ban, defatted soybean, corn, wheat ban and the like.

The composition can be prepared by intimately dispersing or admixing K-41 as the pure compound, a salt, the mycelial cake or broth by methods such as grinding, stirring, milling or tumbling to give compositions of any desired concentration. The composition may include K-41 at a rate of about 0.001 to about 90 weight percent.

The anti-coccidial composition of this invention can be used by mixing with poultry feed or drinking water or administered to poultry directly, e.g. orally. Solutions, suspensions and emulsions are preferrably used with feed or drinking water and capsules and tablets are suited to oral administration. In general, the suitable rate of K-41 in poultry feed is about 0.001 to about 0.5 weight percent and favourably about 0.002 to about 0.012 weight percent. When added to drinking water, the concentration of K-41 may be about 0.0005 to about 0.03 weight percent. K-41 may be orally administered to poultry at a dosage of about 20 to about 200 mg/kg body weight, although the dosage is largely varied depending on particular circumstances such as type and severity of the coccidial infection to be treated.

Furthermore, the compositions may contain other known anti-coccidial agents and parasiticides, if necessary.

The non-toxic salts of K-41 can be also employed as the effective ingredient of the compositions as mentioned above. They are, for example, sodium, potassium, calcium, magnesium, aluminium salts and the like.

Tests of the efficacy of the antibiotic K-41 against *Eimeria tenella* and *Eimeria acervulina* in chicken were carried out and the results are shown below:

Experiment 1

(a) Test method

The chickens, 9-day old broiler chanky, were divided into groups of ten birds and infected with 50,000 sporulated oocysts of *Eimeria tenella* per chicken. The birds were fed with the diet containing the test antibiotic K-41 for 8 consecutive days after infection. On the 8th day, the birds were anatomized and caecal lesions were observed. The number of bloody droppings, survival ratio, relative weight gain, number of oocysts, caecal lesion score and feed conversion ratio were studied during the 8 days.

(b) Results

The results are shown in Table 1.

TABLE 1

| Test Group Concentration in feed (%) | Bloody Droppings | Survival Ratio (%) | Relative Weight Gain (%)[2] | Number of Oocyst[3] | Caecal Lesion Score[4] | Feed Conversion Ratio[5] |
|---|---|---|---|---|---|---|
| X-41 0.012 | — | 100 | 59.2 | 0 | 0 | 2.14 |
| 0.008 | — | 100 | 76.4 | 0 | 0 | 2.03 |
| 0.004 | — | 100 | 96.9 | $1.9 \times 10^4$ | 10 | 1.65 |

TABLE 1-continued

| Test Group Concentration in feed (%) | Bloody Droppings | Survival Ratio (%) | Relative Weight Gain (%)[2] | Number of Oocyst[3] | Caecal Lesion Score[4] | Feed Conversion Ratio[5] |
|---|---|---|---|---|---|---|
| Control (Untreated) | | | | | | |
| Infected | ++ | 100 | 79.1 | $5.6 \times 10^5$ | 26 | 2.25 |
| Uninfected | — | 100 | 100.0 | 0 | 0 | 1.70 |

Notes:
[1] Total count of bloody droppings per group on the 5th and 6th days after the infection are classified as follows: 0: —, 1-5: +, 5-20: ++, more than 20: +++,
[2] Ratio of the increased body weight of infected chickens to that of uninfected chickens
[3] The count of oocysts existing in one gram of feces of chickens on the 8th day after the infection (O.P.G.)
[4] The degree of pathological change in the caeca. Survival chickens were anatomized on the 8th day after the infection and the pathological change of the oaecas was macroscopically degrees The degree of change were classified into 5 orders from 0 (no change) to 4 (seriousness). The figure in the table means total of the score for one group of 10 chickens. (K. Tsunoda and T. Ishii; Method for the examination on the chicken coccidiosis, page 18 (1971).)
[5] The ratio of the feed intake (kg) to body weight gain (kg) during 8 days.

Experiment 2

(a) Test method

The chickens, 9-day old broiler chanky, were divided into groups of ten birds and infected with 500,000 sporulated oocysts of *Eimeria acervulina* per chicken. The birds were fed with diet containing K-41 for 5 consecutive days after infection. Discharge of mucous droppings, survival ratio, relative weight gain, number of oocyst and feed conversion ratio were observed during the five days.

(b) Results

The results are shown in Table 2.

TABLE 2

| Test Group Concentration in feed (%) | Discharge of Mucous Droppings[1] | Survival Ratio (%) | Relative Weight Gain (%)[2] | Number of Oocyst[3] | Feed Conversion Ratio[4] |
|---|---|---|---|---|---|
| K-41 0.012 | — | 100 | 48.4 | $4.4 \times 10^4$ | 2.18 |
| 0.008 | — | 100 | 73.8 | $3.5 \times 10^5$ | 1.69 |
| 0.004 | — | 100 | 83.1 | $2.4 \times 10^6$ | 1.91 |
| Control (Untreated) | | | | | |
| Infected | +++ | 100 | 53.2 | $1.1 \times 10^7$ | 2.27 |
| Uninfected | — | 100 | 100.0 | 0 | 1.88 |

Notes:
[1] The degrees of mucous droppings on the 5th and 6th days were graded as follows: —: regular droppings, +: slightly mucous droppings, ++: medium mucous droppings, +++: seriously mucous droppings
[2] See (2) in the notes of TABLE 1
[3] The count of oocysts (O.P.G.) on the 5th day after the infection
[4] See (5) in the notes of TABLE 1

(c) Conclusion

It is obvious from the above experimental results that K-41 has excellent anti-coccidial activity against *Eimeria acervulina*.

Experiment 3

(a) Test method

The chickens, 9-day old white leghorns, were divided into groups of 10 birds and infected with 50,000 sporulated oocysts of *Eimeria tenella*. The birds were fed with diet containing K-41 or monensin (product of Eli Lilly & Co., Ltd.) for 8 consecutive days after infection. On the 8th day, the birds were anatomized and caecal lesions were observed. The number of bloody discharge, survival ratio, relative weight gain, number of oocyst and feed conversion ratio were studied during the 8 days.

(b) Results

The results are shown in Table 3.

TABLE 3

| Test Group Concentration in feed (%) | Bloody Droppings | Survival Ratio (%) | Relative Weight Gain (%)[2] | Number of Oocyst[3] | Caecal Lesion Score[4] | Feed Conversion Ratio[5] |
|---|---|---|---|---|---|---|
| K-41 0.012 | — | 100 | 96.2 | $5.0 \times 10^4$ | 10 | 1.99 |
| Monensin 0.012 | + | 100 | 82.3 | $2.8 \times 10^5$ | 10 | 2.23 |
| Control | | | | | | |
| Infected | +++ | 80 | 43.0 | $1.5 \times 10^6$ | 40 | 2.41 |
| Uninfected | — | 100 | 100 | 0 | 0 | 2.05 |

Notes:
[1], [2], [3], [4], [5] See the notes in the corresponding number in Table 1

(c) Conclusion

It is obvious from the above results that K-41 shows the superior anti-coccidial activity against *Eimeria tenella* in chickens to monensin, an anti-coccidial agent on the market.

As clearly shown above, K-41 has a powerful anti-coccidial activity. Thus, K-41 can be used to prevent and treat coccidiosis.

The following examples are given solely for the purpose of illustration and are not be construed as limitative of the present invention, many variations of which are possible. In these examples all the percents are given by weight.

EXAMPLE 1

Ten percent of K-41 is admixed with 90 percent of lactose to give a 10-fold trituration. The mixture is diluted with feed to a concentration of 0.001 to 0.05% of the effective ingredient in the feed before use.

EXAMPLE 2

Ten percent of K-41 is admixed with 90 percent of sucrose or starch to give a 10-fold trituration. The mixture is diluted with feed to a concentration of 0.001 to 0.05% of the effective ingredient in the feed before use.

EXAMPLE 3

Ten percent of K-41 is admixed with 90 percent of defatted soybean to give a 10-fold trituration. The mixture is diluted with feed to a concentration of 0.001 to 0.05% of the effective ingredient in feed before use.

EXAMPLE 4

Twenty-five percent of K-41 is admixed with 75 percent of wheat flour to give a powder. The powder is diluted with feed to a concentration of 0.001 to 0.05% of the effective ingredient in the feed before use.

EXAMPLE 5

Forty-five percent of K-41, 12 percent of sucrose, 15 percent of starch, 25 percent of talc, 2 percent of magnesium stearate and 1 percent of stearic acid are admixed.

The mixture is made to granules and pressed into tablets.

EXAMPLE 6

The percent of sodium salt of K-41 is admixed with 90 percent of defatted soybean to give a 10-fold trituration. The mixture is diluted with feed to a concentration of 0.001 to 0.05% of the effective ingredient in feed before use.

EXAMPLE 7

One percent of sodium salt of K-41 is admixed with 99 percent of lactose to give a 100-fold trituration. The mixture is diluted with water to a concentration of 0.005 to 0.03% of the effective ingredient.

What we claim is:

1. A poultry feed composition for controlling coccidiosis in poultry which comprises as an active ingredient about 0.001 weight percent to about 0.5 weight percent of Antibiotic K-41 or a non-toxic salt thereof.

2. A composition according to claim 1, wherein the active ingredient is antibiotic K-41.

3. A composition according to claim 1, wherein the active ingredient is sodium salt of antibiotic K-41.

4. A method for preventing and treating coccidiosis in poultry which comprises feeding an animal with a diet or drinking water containing an anti-coccidially effective amount of antibiotic K-41 or its non-toxic salt.

5. A method according to claim 4 wherein the concentration of K-41 is about 0.001 to about 0.5 weight percent of the feed.

6. A method according to claim 4 wherein the concentration of K-41 is about 0.005 to about 0.03 weight percent of the drinking water.

7. A method for preventing and treating coccidiosis in poultry which comprises administering to an animal an anti-coccidially effective amount of antibiotic K-41 or its non-toxic salt.

8. A method according to claim 7, wherein the amount of K-41 is about 20 to about 200 mg/kg body weight at a time.

* * * * *